(12) United States Patent
Scherlen et al.

(10) Patent No.: US 10,314,476 B2
(45) Date of Patent: Jun. 11, 2019

(54) METHOD FOR DETERMINING VISUAL AID MEANS BY REFERENCE TO THE BEHAVIOUR OF AN INDIVIDUAL SUBJECTED TO A TEST

(71) Applicant: ESSILOR INTERNATIONAL, Charenton-le-Pont (FR)

(72) Inventors: Anne-Catherine Scherlen, Charenton-le-Pont (FR); Géraldine Faure, Marseilles (FR); Miryam Goldschmidt, Pully (CH)

(73) Assignee: ESSILOR INTERNATIONAL, Charenton-le-Pont (FR)

( * ) Notice: Subject to any disclaimer, the term of this patent is extended or adjusted under 35 U.S.C. 154(b) by 0 days.

(21) Appl. No.: 15/750,940

(22) PCT Filed: Aug. 4, 2016

(86) PCT No.: PCT/FR2016/052026
§ 371 (c)(1),
(2) Date: Feb. 7, 2018

(87) PCT Pub. No.: WO2017/029442
PCT Pub. Date: Feb. 23, 2017

(65) Prior Publication Data
US 2018/0228366 A1 Aug. 16, 2018

(30) Foreign Application Priority Data
Aug. 14, 2015 (FR) ...................................... 15 57734

(51) Int. Cl.
*A61B 3/032* (2006.01)
*A61B 3/00* (2006.01)

(52) U.S. Cl.
CPC .............. *A61B 3/032* (2013.01); *A61B 3/005* (2013.01); *A61B 3/0025* (2013.01); *A61B 3/0033* (2013.01)

(58) Field of Classification Search
CPC ..... A61B 3/032; A61B 3/0025; A61B 3/0033; A61B 3/0041; A61B 3/0091
(Continued)

(56) References Cited

U.S. PATENT DOCUMENTS

2006/0078858 A1* 4/2006 Vroman .................... A61B 5/16
434/179
2014/0285769 A1* 9/2014 Palanker ................ G06Q 50/22
351/223
(Continued)

FOREIGN PATENT DOCUMENTS

EP 2 168 473 A1 3/2010
WO 2015/024790 A1 2/2015

OTHER PUBLICATIONS

International Search Report, dated Nov. 15, 2016, from corresponding PCT/FR2016/052026 application.
(Continued)

*Primary Examiner* — Mohammed A Hasan
(74) *Attorney, Agent, or Firm* — Young & Thompson

(57) ABSTRACT

Disclosed is an individual during a specific reading phase. The main feature of a method is that it includes the following steps, a step of subjecting the individual to a test involving the specific reading of a material including a text including a series of common words and into which errors have been inserted between the words at predefined locations, a step in which the individual reads the text out loud, a step of assigning an optical indicator linked to the reading errors identified and making it possible to characterize the quality
(Continued)

of reading, a step of selecting the most appropriate visual aid unit depending on the determined optical indicator.

20 Claims, 2 Drawing Sheets

(58) Field of Classification Search
USPC .......................................................... 351/239
See application file for complete search history.

(56) References Cited

U.S. PATENT DOCUMENTS

| 2016/0147404 | A1* | 5/2016 | Keune | G06F 3/0485 |
| | | | | 715/784 |
| 2016/0198941 | A1 | 7/2016 | Aguilar et al. | |
| 2017/0354324 | A1* | 12/2017 | Bennett | A61B 3/032 |

OTHER PUBLICATIONS

FR Search Report, dated Jun. 6, 2016, from corresponding FR 1 557 734 application.

* cited by examiner

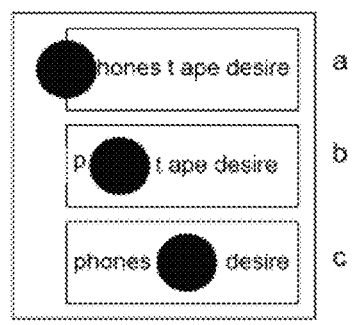
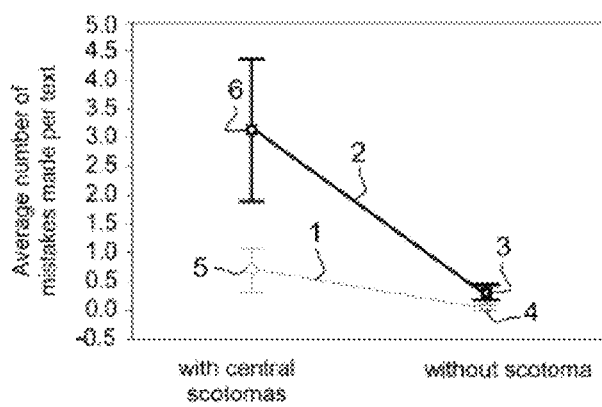

| Subjects | Behavior 0 | Behavior 1 | Behavior 2 | Behavior 3 | Behavior 4 |
|---|---|---|---|---|---|
| Conventional reading test | without | patho | patho | patho | patho |
| | no mistakes | no mistakes | no mistakes | no mistakes | mistakes made in all the sizes of characters |
| Reading test in which a text endowed with defects is read | no mistakes | no mistakes | mistakes made only in small characters | mistakes made in all the sizes of characters | mistakes made in all the sizes of characters |

Reading performance OK; oculo OK (Behavior 0, 1)

Degraded reading performance oculo weakened + re-education strongly advised (Behavior 2, 3, 4)

Fig. 6

METHOD FOR DETERMINING VISUAL AID MEANS BY REFERENCE TO THE BEHAVIOUR OF AN INDIVIDUAL SUBJECTED TO A TEST

BACKGROUND OF THE INVENTION

Field of the Invention

The invention relates to a method for determining visual aiding means with respect to the behavior of an individual who is made to take a test.

More specifically, the invention relates to the design and exploitation of a specific test for evaluating the oculomotile capacities of an individual suffering from a loss of their central field of vision, defined by a visual anomaly of the central scotoma type due for example to age-related macular degeneration (ARMD). Specifically, loss or weakness in central vision degrades oculomotile control, which it is important to be able to detect in order to provide a remedy therefor with suitable correcting means. This oculomotile control may be defined on the basis of parameters related to the movements of the eyes such as for example, saccades, fixations, ocular stability.

The evaluation of the sensorial and oculomotile capacities of an individual is an indispensable datum for understanding and characterizing difficulties the subject has with reading and scene exploration. It also allows an aid with the decision to treat subjects to be determined and consolidated: definition and adaptation of optical and/or electronic visual aiding means and/or provision of a visual re-education, in order to obtain an oculomotile rehabilitation.

A method for determining visual aiding means according to the invention may be used by any type of health professional such as for example opticians, ophthalmologists, orthoptists and doctors, to diagnose the reading capacities of individuals, this essentially depending on ocular motility, but also to help individuals become aware of their visual anomalies and to determine the visual aiding means most suited to the motor sensorial profile of said individuals.

BRIEF SUMMARY OF THE INVENTION

One subject of the invention is a method for determining visual aiding means depending on the behavior of an individual during a specific reading phase.

In the rest of the description, the expression "conventional reading test" corresponds to a reading of a text composed of commonplace words and having an intelligible meaning.

The main feature of a method according to the invention is that it comprises the following steps:
- a step in which the individual is made to take a specific test in which a medium including a text comprising a succession of commonplace words and into which defects have been introduced between said words in predetermined locations is read,
- a step in which the individual reads said text out loud,
- a step in which an optical indicator related to noted reading errors and allowing the quality of the reading to be characterized is attributed,
- a step of selecting the most appropriate visual aiding means depending on the determined optical indicator.

This method aims to reveal a visual anomaly through the reading of a text endowed with defects, then to propose the most suitable correcting means for at least partially remedying this anomaly in order to propose to the individual satisfactory reading conditions. This type of method is particularly suitable for detecting a central scotoma, for example related to an ARMD, the presence of which will mask particular zones of the text and engender a biased reading. An example defect introduced into the text may be the insertion of an isolated letter between two words. The scotoma may then mask, either this isolated letter, or at least one portion of one of the two words flanking this isolated letter. The term "text" is general, and may for example include sequences of commonplace words interspersed with defects, repetitive and easily identifiable patterns, ideograms according to the languages in question. All these constituent elements of the text may be presented with variable and/or constant sizes and/or with a particular arrangement in rows and/or in columns, and/or with varied colors. The individual is supposed to visually decipher the constituent elements of the text. The optical indicator, which may for example take the form of a number optionally associated with a letter, is representative of a visual anomaly and of its amplitude. This indicator is generated in the step of the test in which the text is read, and depends on the number of reading errors noted and on the size of the text in which said errors are made. It is assumed that a correspondence has been established beforehand between the optical index and a visual anomaly. This correspondence may for example be available through a table establishing a correlation between the optical index and a visual anomaly. The visual aiding means may for example take the form of a specific piece of equipment such as a magnifying glass, and have the purpose of at least partially correcting the detected visual anomaly of the individual, in order that he may once again enjoy acceptable reading conditions allowing him to understand a standard text. A database listing for example suitable means for aiding with reading, depending on a particular visual anomaly, may advantageously be used in the context of a determining method according to the invention.

Advantageously, each text defect is chosen from an addition of at least one space, an addition of at least one letter, a removal of at least one space and a removal of at least one letter. These defects remain of minimal dimensions with respect to the dimensions of the commonplace words forming the text.

Preferably, the text comprises a plurality of paragraphs comprising letters of a specific size and a specific spacing between the letters of each word and between the words. In this way, the presence of a plurality of paragraphs having words of different sizes, allows the characteristics of the visual anomaly of the individual to be better characterized.

Preferably, all the paragraphs of the medium have different sizes of letters, and different spacings between the letters of each word and between the words.

Advantageously, the optical indicator is dependent on dimensional characteristics of the paragraphs in which the reading errors were made. The optical indicator takes into account not only the number of errors made during the reading of the text, but also the size of the letters and of the words on which they were made.

Advantageously, the reading medium comprises sequences of identifiable patterns, said sequences being characterized by a succession of groups of patterns each possessing a specific number of patterns and separated from one another by spaces, the spacing between two successive patterns in a group being identical for all the groups. These patterns must not have too complex a geometry and/or outline, as otherwise they might not be identified by the individual. In this way, each pattern may for example be square, round, rectangular, oval or diamond-shaped, or result from a combination of these shapes.

Preferably, the sizes of the spaces interrupting the groups of patterns are different.

Preferably, each sequence comprises identical patterns.

Advantageously, the optical indicator is apt to reveal a visual anomaly consisting of a scotoma and/or an ocular instability. An ocular instability may result from the presence of a scotoma, or may be provoked without particular identifiable cause.

Advantageously, the individual adopts a natural posture during the step of reading the medium. In this way, a method according to the invention is ergonomic and flexible, because it allows an individual to be spared constraining postures that would be liable to disaccommodate him and to bias the conditions under which the text is read.

Preferably, the medium is a screen placed at a predetermined distance from the individual. This screen may for example be that of a television set or of a computer.

According to another preferred embodiment of a method according to the invention, the medium is a manual device that the individual holds while he is taking the reading test. In this way, the individual may modify as he likes the position of the medium in order to obtain a natural reading posture.

Advantageously, a determining method according to the invention comprises a second test in which a medium presenting at least one color is read. Specifically, in order to refine the determination of the visual anomaly, simple and complementary visualization and/or reading tests may be carried out. These complementary tests must be rapid and simple to implement in order not to significantly lengthen a determining method according to the invention.

Advantageously, a determining method according to the invention comprises a third test in which a medium presenting a moving target is read, the path of the moving target being followed visually by the individual. Specifically, in order to refine the determination of the visual anomaly, other simple and complementary visualization and/or reading tests may be carried out.

Preferably, a determining method according to the invention comprises a prior step in which the individual reads a text having a meaning and using commonplace words, the conditions under which the step in which the specific test is taken depending on reading errors noted in said prior step. Specifically, if the individual has already made reading errors in this preliminary reading test, the individual will possibly be asked to read directly a particular zone of the text with defects, corresponding to a particular size of letter and/or defects.

Preferably, a determining method according to invention comprises a step of producing a table of optical criteria, comprising at least three distinct and identifiable categories, a first category corresponding to normal vision, a second category for which the vision presents a few anomalies and a third category for which the vision presents a large number of anomalies. Depending on the sought-after visual-anomaly-detection refinement, subdivisions of categories may be envisioned.

Advantageously, each category is referenced by a number and/or a letter that depends on the characteristics of the detected visual anomalies.

Advantageously, a determining method according to the invention comprises a step of recording the table of optical criteria. In this way, this table is available at any moment. Preferably, this lookup table may be displayed on a screen.

Preferably, a determining method according to the invention comprises a step of building a database establishing a correlation between the optical index and the most suitable means for aiding with a visual correction. This database may establish, either a direct correlation between the optical index and the means for aiding with reading in order to at least partially remedy the visual anomaly, or a correlation between a visual anomaly and said means for aiding with reading.

Preferably, the means for aiding with vision are chosen from magnifying glasses, microscopic spectacles, telescopic systems of the Galilean or Keplerian type, portable electronic aids, electronic aids of the TV-video-magnifier type, lamps, filters, spectacles equipped with augmented reality means, progressive lenses of high addition and oculomotile re-education sessions.

Another subject of the invention is a device for carrying out a determining method according to the invention.

The main feature of a device according to the invention is that it consists of a mobile digital terminal possessing a suitable software package and an access to recorded databases.

Advantageously, the mobile digital terminal is a touch tablet able to make the reading medium appear and to record the voice of the individual, said tablet possessing an optical-index-determining software package, and a lookup table describing the correspondence between said optical index and the corresponding visual anomaly, said tablet furthermore possessing an access to databases establishing a correlation between said optical index and the most suitable visual aiding means.

A method for determining visual aiding means according to the invention has the advantage of being able to be applied both to one eye and to both eyes. It is frequent in the treatment of visual impairment to provide pieces of monocular or binocular optical equipment depending on the sensorial or oculomotile rivalry of the two eyes. In other words, seeing or reading with both eyes may be more disadvantageous for a reader. Thus, a piece of monocular equipment may allow a better performance to be obtained. It in addition has the advantage of being easy and rapid to implement, and of allowing an individual to adopt a natural reading posture. In this way, the results of the method will not be biased by constraining reading postures liable to alter the principle of said method.

BRIEF DESCRIPTION OF THE DRAWINGS

A detailed description of a preferred embodiment of a determining method according to the invention is given below with reference to the following figures:

FIG. 1 is a view of a first example text and of a spot embodying a visual anomaly, FIG. 2 is a view of a second example text and of a spot embodying a visual anomaly, FIGS. 3a, 3b, 3c are three views of the same text endowed with defects and of a spot embodying a visual anomaly in three different positions on said text, FIG. 4 is an example of a text endowed with defects and suitable for the implementation of a determining method according to the invention, FIG. 5 is a comparative plot of the number of reading errors made with an intelligible text and with a text endowed with defects, with or without the presence of a visual anomaly, FIG. 6 is an example of a summary table showing various categories each corresponding to one behavior reading an intelligible text and a text endowed with defects.

DETAILED DESCRIPTION OF THE PREFERRED EMBODIMENTS

Certain individuals possess visual anomalies, such as for example a scotoma and/or an optical instability, which may have major repercussions, in particular in the reading of a text.

Specifically, with reference to FIGS. 1 and 2, the presence of a central scotoma masks reading zones that may be of relatively large size, depending on the size of the letters of the text, on the spacing between the words, on the spacing between the lines, etc. . . .

With reference to FIG. 1, when the size of the characters is large, it remains possible to guess the words disfigured by the presence of the scotoma, but this nevertheless requires a substantial intellectual effort to be made, which it appears is difficult to maintain over the entirety of a text or a book.

In contrast, with reference to FIG. 2, when the size of the characters is too small, an intelligible reading of a text remains almost impossible.

Generally, reading with a central scotoma disrupts reading processes: decrease in visual acuity and sensitivity to contrasts and loss of central motor frame of reference. Oculomotile control is the most rapid, the most precise and the most stable in central vision. The presence of a central scotoma leads to peripheral fixation i.e. what is known as eccentric fixation. This loss of frame of reference leads inter alia to an increase in fixation instability and to a decrease in the amplitude of the saccades, thus limiting reading effectiveness.

In addition, when a person reads with a scotoma, some of the visual information is masked. He will have to move his eye and thus his scotoma in order to unmask the letters of the words in order to read them.

Unfortunately, instabilities in the eye or the loss of clues as to the shape of the words (low-level process of recognition of words) decreases the time for recognition of the text. In addition, it is very frequent that the patient, even if he does not see all the letters of the words, as a result of difficulty moving his eyes, uses the semantic context of the text to guess the words. The cognitive load associated with this strategy is high and it is very frequent that the reader runs up against an inconsistency in his reading after a few sentences have been read. The reader will become tired with reading, his reading speed will decrease and he will become discouraged and may even abandon his attempt.

With a view to effective treatment, it is indispensable to know the actual reading strategies of subjects and to determine the way in which the subject makes so as to be able to read effectively with the constraint of the presence of a central scotoma or with a loss of central vision.

A method for determining a visual behavior according to the invention aims to detect a visual anomaly of the scotoma type and then to evaluate the ability to move and control ocular movements, in order to propose the visual aid that is most suited to the characteristics of this anomaly.

In the following detailed description, the example visual anomaly considered is a central scotoma.

A method for determining a visual aid depending on the behavior of an individual during a specific reading phase, comprises the following steps:

A—a step in which the individual is made to take a specific test in which a medium including a text comprising a succession of commonplace words and into which defects have been introduced between said words in predetermined locations is read. Generally, the text is formed in the following way, Successions of words without meaning therebetween: the individual cannot use the context to guess the words, Use of isolated letters to create confusion between the words: if the subject cannot see the space between the isolated letter and the word, he may say another word i.e. one that is not displayed. The choice of the words and of the isolated letters will have been judiciously made to push the subject into making errors.

Choice of words that can be read without the first or the last letter in order to induce confusion, or allow interpretation of mistakes made by the reader, With reference to FIGS. 3a, 3b, 3c a first example of a text into which defects have been introduced may consist of a paragraph composed of a plurality of superposed lines. Each line thus consists of a succession of commonplace words interspersed with defects each consisting of the insertion of a single letter between said words. This insertion is not regular. In this way, two commonplace words may be placed one directly after the other. Depending on the position of the occulting spot caused by the scotoma within a given succession of words endowed with defects, the reading will be completely different. Thus, the reading of the words appearing in FIG. 3a will be completely different from that of the words appearing in FIG. 3b, and different from that of the words appearing in FIG. 3c. Because of the insertion of these defects into the text, the successions of words are devoid of sense, and the individual afflicted with this visual anomaly cannot therefore surmise intellectually the missing letters in order to attempt to give a sense to this succession of words.

With reference to FIG. 4, a second example of a text into which defects have been introduced may consist of a plurality of paragraphs, in the present case three paragraphs, each having different sizes of letters and a different spacing between said letters. Thus, a first paragraph is written in large letters and possesses three superposed lines, each line consisting of a succession of commonplace words interspersed with isolated letters that form the defects introduced into the text. These isolated letters are each placed between two commonplace words. However, all the sequences of two successive commonplace words do not systematically have an isolated letter inserted between them. The size of all the letters forming this first paragraph is constant, as is the spacing between the letters of a commonplace word and the spacing between two commonplace words and between an isolated letter and a commonplace word. A second paragraph having the same structural characteristics as the first paragraph is written with medium letters, the size of which is smaller than that of the letters of the first paragraph. A third paragraph having the same structural characteristics as the first and second paragraphs is written with small letters, the size of which is smaller than that of the letters of the second paragraph.

A third example of a text into which defects have been introduced may consist in replacing the letters with identifiable patterns having a simple geometry, such as for example a square, rectangular or diamond-shaped geometry. In this way, each sentence would appear in coded form, with sequences of patterns interspersed with spacings of relatively large size, the spacing between the patterns of a given sequence being constant.

B—a step in which the individual reads said text out loud. This step of reading out loud is indispensable for detecting the errors that the individual may make reading the text endowed with its defects. According to one variant embodiment of the invention, this reciting step may be done in writing.

C—a step of noting these defects. This step may be carried out automatically by means of an apparatus able to detect the sounds emitted during an out-loud reading and to instantaneously and automatically note reading errors via comparison with a pre-recorded reference reading. The errors may also be noted manually by a third person who also has access to the reading text.

D—an optional step in which the individual reads an intelligible text consisting of sentences of commonplace words and having a meaning. This optional step may be implemented at any moment during a determining method according to the invention. Preferably, it consists of a step prior to the step of reading the text endowed with defects. Specifically, this optional step is easy and rapid to implement, because the reading errors made by the individual may be detected even without having access to the text. It is enough to listen to what the individual says when reading the text to know whether he is making many, few or no errors. FIG. 5 demonstrates how important a determining method according to the invention is with respect to revealing the presence of a scotoma relative to a conventional reading test in which a coherent and intelligible text is read. Curve 1 relates to a reading test in which a text possessing defects is read, and curve 2 relates to a reading test in which a coherent and intelligible text is read. The two points 3, 4 of these two curves located on the right represent the average number of reading errors made by an individual without a scotoma. For these two points, the two reading tests give about the same result, namely less than 0.5 reading mistakes. The two points 5, 6 of these two curves located on the left represent the number of reading errors made by an individual with a central scotoma. For the reading test in which the coherent and intelligible text is read, the number of reading errors 5 remains low, lower than 1. In contrast, the number of reading errors 6 when the text possessing defects is read is much higher, about three. Such a difference in results reveals how important a determining method according to the invention is with respect to detecting a visual anomaly of the central scotoma type. The reading test in which a coherent and intelligible text is read assists with implementation of a method according to the invention. If, by way of example, an individual makes an unusual number of errors during the conventional reading test, he will then possibly be asked to start the test in which the text endowed with defects is read, on a paragraph having letters of medium or large size.

E—a step in which an optical indicator related to the noted reading errors and allowing the quality of the reading to be characterized is attributed. Reading quality encompasses not only reading ability but also the associated interpretation. This indicator depends on the number of reading mistakes and on the location of the mistakes given the size of the letters of the paragraph read.

It will be noted that the reading test in which a text possessing defects is read, and the accompanying analysis of reading mistakes, in addition allows the reading acuity of the individual to be evaluated, any difficulty he has moving his scotoma to be evaluated, and indirectly his oculomotile capacity to be determined.

With reference to FIG. 6, the results of the reading test in which a text comprising defects is read may be presented in the form of a plurality of categories, each being representative of the number and location of the reading mistakes in the text read. The example table illustrated in FIG. 6 simultaneously gives the results of a conventional reading test and of a reading test in which a text comprising defects is read. In this example, a first category is for example defined in which the individual makes no reading mistakes in both tests, leaving it to be believed that the individual possesses no scotoma. A second category corresponds to an absence of reading mistakes, even though the individual does possess a scotoma. A third category corresponds to no mistakes in the conventional reading test and to mistakes being made only in the small characters during a reading test in which a text possessing defects is read. A fourth category corresponds to no mistakes in the conventional reading test and to mistakes being made in all the sizes of characters during a reading test in which a text possessing defects is read. A fifth category corresponds to reading mistakes in all the sizes of characters during a conventional reading test and to mistakes being made in all the sizes of characters during a reading test in which a text possessing defects is read. The optical index, which may for example take the form of a number and/or a letter, is representative of the categories defined above. This index reflects reading errors made by the individual and therefore the quality of his visuo-oculomotile coordination. According to one variant embodiment of the invention, the index may also take into account the distribution of the errors made reading the text, for example errors detected more at the center than on the edges of the paragraphs. The behavior corresponding to the fourth category above is typically the most important behavior to diagnose in a clinical setting. The individual makes no mistakes with the conventional test, whereas a real oculomotile problem is encountered in the reading test in which a text possessing defects is read. In a test carried out with 70 individuals, 36% of the individuals were classified into this fourth category, and 21% into the fifth category. The behaviors of the fourth and fifth categories require a specific treatment, from the oculomotile point of view, in addition to a sensorial treatment, in terms of visual acuity and sensitivity to contrasts.

The type of behavior is independent of visual acuity and the location of the eccentric fixation, but is dependent on the value of the fixation instability.

F—a step of selecting the most appropriate visual aiding means depending on the determined optical indicator.

To select the right visual aid, it is important to determine characteristics of the vision of the individual that are related to the reading of a text, and that depend mainly, apart from on his identification capacities, on his visual acuity, oculomotile capacities and the interaction between the latter two. The choice of the most suitable visual aid will be made depending on these 3 characteristics.

The acuity test known as the dynamic acuity test, which evaluates the ability of the wearer to move his scotoma during the exploration of a text, allows the reading acuity of the wearer to be more effectively determined and a preciser value to be obtained for the magnification that should be used for the piece of equipment for aiding with vision that is right for the individual. If these capacities are diminished, the magnification of the piece of equipment for aiding with vision that is right for the individual will have to be increased accordingly. This test may be carried out with a text medium or indeed with programmed information-technology means such as a computer, smartphone or tablet.

The visual acuity test is for example carried out by displaying 12 rows of letters. Each row of letters is composed of five capital letters. The letters used are the letters called Sloan letters, i.e. S, O, C, D, K, V, R, H, N, Z, as described in the work "Borish's Clinical Refraction", by William J. Benjamin, published in 2006 by Butterworth-Heinemann/Elsevier. Specifically, these letters are easily recognizable. In a language different from English, and in particular in a language using a different alphabet, all the letters of the alphabet could be used or a different group of letters.

In each row, the size of the letters corresponds to a visual angle of discrimination, i.e. to a determined visual acuity. The size of the letters decreases from the first to the last row.

The size of the letters is for example calibrated for a reading distance of 40 cm. The tested range of visual acuity here depends in part on the resolution characteristics of the touchscreen used. It is possible with present-day screens to display rows of letters allowing visual acuities comprised between 5/10 and 1/25 to be tested. Preferably, the visual-acuity interval between each row is constant, this allowing a regular and refined measurement whatever the tested visual-acuity range. For a given row, the spacing between two letters is equal to the size of the letters of this row.

If the test is made up of sentences, the words of the selected sentences are preferably selected to be words that are simple to understand. These sentences are for example taken from a well-known text such as a story or fable. The words composing these sentences may also be chosen depending on how frequently they occur in the language in question. These frequencies of occurrence are determined via scientific studies. In French for example, the results of such a study may be found at the following Internet address: http://www.lexique.org. It is preferably a question of the words that are the most frequently used in the language in question. Each sentence preferably comprises between 10 and 15 words, the words being divided uniformly between short words, containing 2 letters or less, words of medium lengths, containing between 3 and 5 letters and long words, containing more than 5 letters.

The ocular motility test makes it possible to determine whether the eyes of the wearer are able to move with the same agility in every direction. To this end, it is possible to use a test in which a text is read or a target tracked. The ocular motility test also allows the stability of the ocular fixation to be determined. A target for example having the shape of a cross and dimensions and contrasts suitable for the visual acuity of the wearer is displayed in the center of the screen. A video camera records and follows the movements of the center of the eye, and more particularly the luminous corneal reflection provoked by the presence of a point light source, for example a light-emitting diode, that is directed onto the eye according to a gaze-tracking technique that is known per se. The quality of the ocular fixation is evaluated by demanding the person to fixate on the center of the cross for 30 seconds. A video camera records the variations in the position of the corneal reflection during the test. Thus, whether the movements of the eye are continuous or discontinuous is determined. The measurement may be carried out for monocular or binocular vision.

The evaluation of the oculomotile quality has an impact on the choice of the aid, and more specifically on the visual field associated with the piece of equipment. A wearer with a high ocular fixation instability will be more comfortable and achieve a higher performance level if the piece of equipment chosen for the individual has a large field of vision. A piece of equipment of the TV-video-magnifier type would for example in such a case be preferable to a piece of equipment of the Galilean-system type because the former has a much larger field of vision.

In our case, it is a question, by way of a specific acuity test, such as for example a conventional reading test, of determining characteristics of the vision of the individual that are related to reading while taking into account his visual acuity and his oculomotile capacities.

The field of vision may be limited by the presence of a "blind" spot called a scotoma. Visually impaired people for example having such a scotoma in their field of vision may frequently present defects in coordination that lead them to interpret and also an irregular ocular stability because they will seek to use both their peripheral vision and repeated movements of their eyes in a number of (almost horizontal for example) directions to enlarge their field of vision of the word. This characteristic related to the vision of the individual plays an important role in the choice of the piece of equipment for aiding with vision.

Beforehand, the user will possibly read a uniform and ordered series of texts by way of a phase of training and increasing the confidence of the individual. This makes it possible to check that the individual has indeed understood the instructions of the operator.

Then it is a question of inserting, in a predetermined way into the series of displayed words, additional letters, or of removing letters or indeed of creating spaces so as to cause an individual applying a strategy involving rote learning or an interpretation of what is being read to fail. The defects assimilated or not detected by the individual during the reading are then detected.

This test allows the quality of the individual's coordination when reading to be characterized, and a reading indicator taking into account both the acuity test and the ocular motility test to be determined in a simple and ergonomic fashion, with a view to optimizing the choice of the visual aid.

The presence of a fixation instability is an indicator of decline in performance in a reading phase or an exploring task i.e. when reading but also in other exploration-type activities.

In the case of treatment of people with central scotomas, the choice and parameterization of the aids will be different depending on whether oculomotile difficulties are present:

If oculomotor weaknesses are present:
  a visual aid with a large field is preferred. There is a link between the degree of fixation instability and the size of the field of the aid to be proposed with a view to optimizing performance levels. Visual comfort and reading performance/effectiveness are higher. A Galilean system (small field) is to be avoided with respect to an electronic magnifier, the field of projection of the image of electronic magnifiers being larger.
  visual re-education is suggested, with the aim of improving the stability of the eye. A decrease in the number of mistakes in the conventional reading test has been observed after about ten oculomotile re-education sessions. An improvement in fixation stability decreases the number of mistakes made in this test.
In the case of parameterization of progressive lenses such as defined in standard ISO 13666:2012, the specifications of a progressive lens design may be set depending on the degree of instability of the eye. It is possible to imagine the width of the clear-vision column being tailored to the value of the fixation instability.

The following is a nonexhaustive list of some visual aiding means allowing the presence of a visual and oculomotile anomaly related to the presence of scotomas to be mitigated:
magnifying glasses,
microscopic spectacles,
telescopic systems of the Galilean or Keplerian type,
portable electronic aids,
electronic aids of the TV-video-magnifier type,
lamps,
filters,
spectacles equipped with augmented reality means,
progressive lenses of high addition,
an oculomotile and visuo-oculomotile re-education.

The invention claimed is:

1. A method for determining a visual aid depending on the behavior of an individual during a specific reading phase, the method comprising:
   a step in which the individual is made to take a specific test in which a medium including a text comprising a succession of commonplace words and into which defects have been introduced between said words in predetermined locations is read, said defects introducing disruptions apt to make a text devoid of sense and/or apt to break the harmony of a sequential and repetitive structure of a pattern,
   a step in which the individual reads said text out loud,
   a step in which an optical indicator related to noted reading errors and allowing the quality of the reading to be characterized is attributed, and
   a step of selecting the most appropriate visual aiding means depending on the determined optical indicator.

2. The determining method as claimed in claim 1, wherein each text defect is chosen from an addition of at least one space, an addition of at least one letter, a removal of at least one space and a removal of at least one letter.

3. The determining method as claimed in claim 2, wherein the reading medium comprises sequences of identifiable patterns, said sequences being characterized by a succession of groups of patterns each possessing a specific number of patterns and separated from one another by spaces, and wherein the spacing between two successive patterns in a group is identical for all the groups.

4. The determining method as claimed in claim 3, wherein each sequence comprises identical patterns.

5. The determining method as claimed in claim 1, wherein the text comprises a plurality of paragraphs comprising letters of a specific size and a specific spacing between the letters of each word and between the words.

6. The determining method as claimed in claim 5, wherein all the paragraphs of the medium have different sizes of letters, and different spacings between the letters of each word and between the words.

7. The determining method as claimed in claim 6, wherein the optical indicator is dependent on dimensional characteristics of the paragraphs in which reading errors were made.

8. The determining method as claimed in claim 1, wherein the optical indicator is apt to reveal a visual anomaly consisting of a scotoma and/or an ocular instability.

9. The determining method as claimed in claim 1, wherein the individual adopts a natural posture during the step of reading the medium.

10. The determining method as claimed in claim 1, wherein the medium is a screen placed at a predetermined distance from the individual.

11. The determining method as claimed in claim 1, further comprising a prior step in which the individual reads a text having a meaning and using commonplace words, and wherein the conditions under which the step in which the specific test is taken are dependent on reading errors noted in said prior step.

12. The determining method as claimed in claim 1, further comprising a step of producing a table of optical criteria, comprising at least three distinct and identifiable categories, a first category corresponding to normal vision, a second category for which the vision presents a few anomalies and a third category for which the vision presents a large number of anomalies.

13. The method for determining claim 12, further comprising a step of recording the table of optical criteria.

14. The determining method as claimed in claim 1, further comprising a step of building a database establishing a correlation between the optical index and the most suitable means for aiding with a visual correction.

15. The determining method as claimed in claim 1, wherein the means for aiding with vision are chosen from magnifying glasses, microscopic spectacles, telescopic systems of the Galilean or Keplerian type, portable electronic aids, electronic aids of the TV-video-magnifier type, lamps, filters, spectacles equipped with augmented reality means, progressive lenses of high addition and oculomotile re-education sessions.

16. A device for carrying out a determining method as claimed in claim 1, the device comprising a mobile digital terminal possessing a suitable software package and an access to recorded databases.

17. The device as claimed in claim 16, wherein the mobile digital terminal is a touch tablet able to make the reading medium appear and to record the voice of the individual, and wherein said tablet possesses an optical-index-determining software package, and a lookup table describing the correspondence between said optical index and the corresponding visual anomaly, said tablet furthermore possessing an access to databases establishing a correlation between said optical index and the most suitable visual aiding means.

18. The determining method as claimed in claim 1, wherein said defects introducing disruptions apt to make the text devoid of sense and/or apt to break the harmony of the sequential and repetitive structure of a pattern are defects selected for detecting a scotoma in the individual.

19. A method for determining a visual aid depending on the behavior of an individual during a specific reading phase, the method comprising:
   a step in which the individual is made to take a specific test in which a medium including a text comprising a succession of commonplace words and into which defects have been introduced between said words in predetermined locations is read, said defects introducing disruptions apt to make a text devoid of sense and/or apt to break the harmony of a sequential and repetitive structure of a pattern;
   a step in which the individual reads said text out loud;
   a step in which an optical indicator related to noted reading errors and allowing the quality of the reading to be characterized is attributed; and
   a step of selecting the most appropriate visual aiding means depending on the determined optical indicator,
   wherein the text comprises a plurality of paragraphs comprising letters of a specific size and a specific spacing between the letters of each word and between the words, and
   wherein the optical indicator is dependent on dimensional characteristics of the paragraphs in which reading errors were made.

20. A method for determining a visual aid depending on the behavior of an individual during a specific reading phase, the method comprising:
- a step in which the individual is made to take a specific test in which a medium including a text comprising a succession of commonplace words and into which defects have been introduced between said words in predetermined locations is read, said defects introducing disruptions apt to make a text devoid of sense and/or apt to break the harmony of a sequential and repetitive structure of a pattern;
- a step in which the individual reads said text out loud;
- a step in which an optical indicator related to noted reading errors and allowing the quality of the reading to be characterized is attributed; and
- a step of selecting the most appropriate visual aiding means depending on the determined optical indicator,
- wherein the reading medium comprises sequences of identifiable patterns, said sequences being characterized by a succession of groups of patterns each possessing a specific number of patterns and separated from one another by spaces, and wherein the spacing between two successive patterns in a group is identical for all the groups.

* * * * *